United States Patent
Philbrook et al.

(10) Patent No.: US 7,022,343 B2
(45) Date of Patent: Apr. 4, 2006

(54) CONTROLLED RELEASE OF ANTI-ARRHYTHMIC AGENTS

(75) Inventors: C. Michael Philbrook, Boston, MA (US); James W. Burns, Watertown, MA (US); Kevin C. Skinner, Andover, MA (US); Robert J. Miller, Quincy, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/033,274

(22) Filed: Dec. 27, 2001

(65) Prior Publication Data
US 2002/0150622 A1    Oct. 17, 2002

Related U.S. Application Data

(60) Provisional application No. 60/258,369, filed on Dec. 27, 2000.

(51) Int. Cl.
*A61K 9/00* (2006.01)
*A61K 9/14* (2006.01)

(52) U.S. Cl. ............ 424/484; 424/400; 424/422; 424/425; 424/488

(58) Field of Classification Search ............ 424/484, 424/488, 422, 400, 425
See application file for complete search history.

(56) References Cited

U.S. PATENT DOCUMENTS

| | | | |
|---|---|---|---|
| 4,243,775 A | 1/1981 | Rosensaft et al. | |
| 4,526,938 A | 7/1985 | Churchill et al. | |
| 5,387,419 A * | 2/1995 | Levy et al. | 424/422 |
| 5,410,016 A | 4/1995 | Hubbell et al. | |
| 5,567,435 A | 10/1996 | Hubbell et al. | |
| 5,650,447 A | 7/1997 | Keefer et al. | |
| 5,779,673 A | 7/1998 | Roth et al. | |
| 5,800,373 A | 9/1998 | Melanson et al. | |
| 5,834,274 A | 11/1998 | Hubbell et al. | |
| 5,844,016 A | 12/1998 | Sawhney et al. | |
| 5,900,245 A * | 5/1999 | Sawhney et al. | 424/426 |
| 5,947,977 A | 9/1999 | Slepian et al. | |
| 5,986,043 A | 11/1999 | Hubbell et al. | |
| 6,060,582 A | 5/2000 | Hubbell et al. | |
| 6,083,524 A | 7/2000 | Sawhney et al. | |
| 6,121,341 A | 9/2000 | Sawhney et al. | |
| 6,123,667 A | 9/2000 | Poff et al. | |
| 6,177,095 B1 | 1/2001 | Sawhney et al. | |
| 6,197,324 B1 | 3/2001 | Crittenden | |

(Continued)

FOREIGN PATENT DOCUMENTS

WO    WO 94/21237    9/1994

(Continued)

OTHER PUBLICATIONS

US Pharmacopoeia (USP 24/NF 19), p. 2254, (2000).

(Continued)

*Primary Examiner*—Thurman K. Page
*Assistant Examiner*—Simon J. Oh
(74) *Attorney, Agent, or Firm*—Isabelle A. S. Blundell

(57) ABSTRACT

Methods for the simple, reliable application and local controlled release of selected anti-arrhythmia drugs from a hydrogel applied to or polymerized on the tissues of the heart or its vessels, especially in conjunction with cardiac bypass or other cardiac surgery, have been developed. The anti-arrhythmia drugs are incorporated into hydrogels that biodegrade and adhere to the tissues to which the anti-arrhythmic drugs are to be delivered. The hydrogels may be formed in vitro or in vivo. In a preferred embodiment, the drugs are effective to lengthen atrial effective refractory period. A particularly preferred drug is amiodarone.

7 Claims, 5 Drawing Sheets

U.S. PATENT DOCUMENTS

| | | | |
|---|---|---|---|
| 6,306,922 B1 | 10/2001 | Hubbell et al. | |
| 6,605,294 B1 * | 8/2003 | Sawhney | 424/426 |
| 6,632,457 B1 | 10/2003 | Sawhney | |
| 2003/0009145 A1 | 1/2003 | Struijker-Boudier et al. | |

FOREIGN PATENT DOCUMENTS

| | | |
|---|---|---|
| WO | WO 02/16442 | 2/2002 |
| WO | WO 02/16442 A2 * | 2/2002 |

OTHER PUBLICATIONS

Barman. et al., "Thermoresponsive, Biodegradable Hydrogels; Effect of Chain Structure on Hydrogel Properties", 23$^{rd}$ Annual Meeting of the Society For Biomaterials, Apr. 30-May 4, 1997, p. 120.

Barman, et al., "Sustained Release from Bioabaorable Polyether-based Matrices with Variable Chain Segments", 23rd Annual Meeting of the Society For Biomaterials, Apr. 30-May 4, 1997, p. 194.

Ayers, et al., "Amiodarone Instilled Into the Canine Perlcardial Sac Migrates Transmurally to Produce Electrophysiologic Effects and Suppress Atrial Fibrillation", J. Cardiovasc. Electrophysiol., 7(8);713-721 (1986).

* cited by examiner

CONTROLLED RELEASE OF ANTI-ARRHYTHMIC AGENTS

CROSS-REFERENCE TO RELATED APPLICATIONS

This application claims priority to U.S. Provisional Application No. 60/258,369 filed Dec. 27, 2000.

BACKGROUND OF THE INVENTION

The present invention is generally in the field of controlled drug delivery, and particularly in the area of direct delivery of anti-arrhythmic agents to the surface of the heart and its associated tissues.

Coronary artery bypass graft (CABG) surgery is a standard surgical that procedure that replaces clogged or degraded cardiac arteries. However, the act of operating on the heart can disturb the regulation of the heartbeat. Post-surgical arrhythmias resulting from this disturbance can complicate the recovery process and can be fatal.

Atrial fibrillation is the most common postsurgical arrhythmic event following open heart surgery. Postoperative atrial fibrillation has been found to occur following approximately 20–30% of all CABG and valve procedures, and usually occurs within 10 days following surgery. Anti-arrhythmic drugs typically are administered orally or by IV either to treat atrial fibrillation when it occurs or as a prophylactic therapy. However, systemic administration of anti-arrhythmic agents is not always desirable or practical.

Administration of anti-arrhythmic agents to cardiac tissue, directly or on a pacemaker lead, has been proposed in U.S. Pat. No. 5,387,419 and WO 94/21237 to Levy and Sintov. U.S. Pat. No. 5,387,419 describes the direct application of anti-arrhythmic agents in a carrier. However, this application has proven to be impractical because the carriers are not tissue adherent and do not bioresorb. For example, U.S. Pat. No. 5,387,419 describes placing lidocaine in polyurethane, which must be prepared outside the body at 60° C. and then sutured to the heart.

There is a need for more practical methods of administration of anti-arrhythmic agents.

It is therefore an object of this invention to provide controlled delivery of anti-arrhythmic drugs through the direct application of tissue adherent polymeric hydrogel matrices.

SUMMARY OF THE INVENTION

Methods for the simple, reliable application and local controlled release of selected anti-arrhythmic drugs to tissues of the heart or blood vessels, especially in conjunction with cardiac bypass or other cardiac surgery, have been developed. The anti-arrhythmia drugs are incorporated into hydrogels that adhere to the tissues to which the anti-arrhythmic drugs are to be delivered and then biodegrade. The hydrogels compositions and patches containing anti-arrhythmic drugs may be formed in vitro or in vivo. The hydrogels are particularly well suited for the delivery of poorly soluble drugs, such as amiodarone. Preferred hydrogels are tissue adherent and biodegradable within seven to ten days following application. Most preferred hydrogels are formed of synthetic polymers that provoke minimal inflammation or fibrosis. The hydrogels can be applied directly to the tissue where drug delivery is desired, by spraying or painting the gel onto the tissue, or in the form of a "patch" that provides a defined dosage of drug for release at the site of application.

As demonstrated by the examples, in a preferred embodiment, hydrogels that are formed by photopolymerization of a diacrylated polyethyleneglycol macromer containing hydrolysable linkages (FOCALSEAL™) provide effective delivery of anti-arrhythmic drugs such as amiodarone applied directly to the atrium in animal models including dogs and pigs to increase the atrial effective refractory period ("AERP"). The hydrolysable linkages are either lactide-trimethylenecarbonate oligomers or trimethylenecarbonate oligomers, that are cleaved by hydrolysis following application, degrading into simple metabolic products that are non-toxic.

DETAILED DESCRIPTION OF THE INVENTION

I. Compositions

Figure 1:
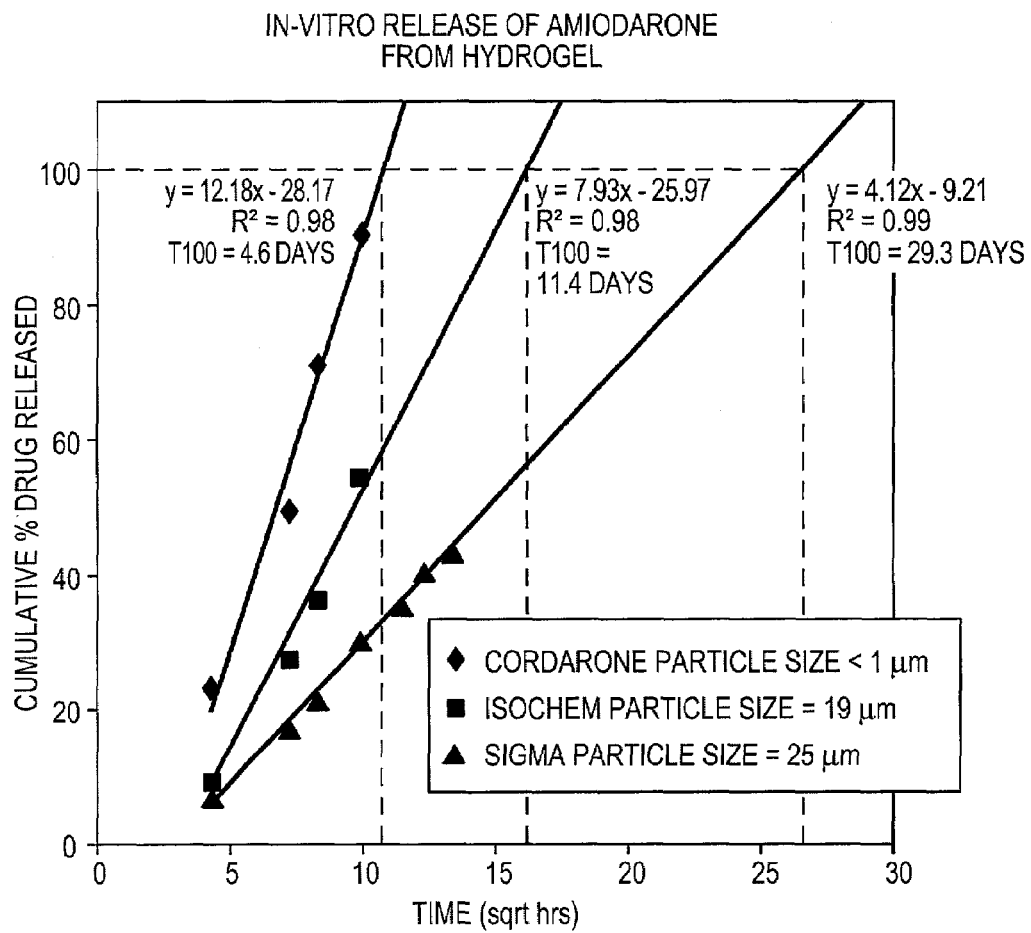
FIG. 1 is a graph of the temporal release of amiodarone from hydrogels (cumulative percent (%) of amiodarone released over time in the square root of hours). It depicts the release of amiodarone in three different particle sizes, 25 μm (▲), 19 μm (■), and less than 1 μm (◆).

The compositions contain a biocompatible, polymeric hydrogel matrix that is tissue adherent and preferably degrades in a period of time minimizing tissue inflammation, for example in less than seven to ten days, and an anti-arrhythmic agent, preferably in an amount effective to lengthening the atrial effective refractory period ("AERP").

A. Hydrogel Matrix

To achieve the above properties, the hydrogel is formed primarily of polymerized macromers, the macromers being themselves polymers or copolymers of one or more monomers having reactive groups providing resorbable linkages and polymerizable sites for biodegradability and polymerization. The macromers have sufficient hydrophilic character to form water-absorbent polymerized gel structures, and are at least dispersible in a substantially aqueous solution, and preferably are water-soluble, to maximize tissue adherence. The macromers are preferably made predominantly of synthetic materials. The resulting hydrogels are preferably highly compliant, so as not to impede the process of cardiac contraction. The hydrogels are preferably covalently crosslinked to ensure that they are retained at the site of application until the hydrogels degrade.

Monomer and Macromer Components of the Hydrogel

Monomers and macromers which are suitable for forming the hydrogels ("referred to here in this section collectively as "monomers") have one or more of the following properties: water soluble, partially macromeric character, containing hydrophilic groups, and being covalently reactive. When crosslinked to form gels, the resulting gels are tissue adhesive, elastic, and compliant. The monomers are preferably water soluble. Water soluble materials are soluble to at least about 0.1 gram per liter of a substantially aqueous solvent. A substantially aqueous solvent comprises at least about 50% by weight of water, and less than about 50% by weight of a non-aqueous, water-miscible solvent. If the polymers are not entirely water soluble, they should be dispersible in water, and form micelles, typically with the aid of non-aqueous, water-miscible solvents. The non-aqueous solvent must be present in an amount that does not damage the tissue. Thus only a small amount of non-aqueous, water-miscible solvent should be present in the pre-gelled composition to minimize tissue irritation. Up to about 10% by weight of the solution can be a non-aqueous, water-miscible solvent. Examples of non-aqueous, water-miscible solvents include ethanol, isopropanol, N-methylpyrrolidone, propylene glycol, glycerol, low molecular weight polyethylene glyco, DMSO, Benzyl alcohol, and benzyl benzoate. Liquid surfactants, such as poloxamers (e.g., PLURONIC™ surfactants) and some polyethylene glycol derivatives (e.g., some TWEEN™ surfactants) can also be used as non-aqueous, water-miscible solvents.

The monomers are preferably at least partially macromeric, and are more preferably substantially to completely macromeric. Macromers tend to be innocuous to tissue because they will not readily diffuse into or penetrate cells. A macromer is a reactive monomer consisting of a polymeric material with a number-average or weight-average molecular weight of about 500 Daltons or more and at least one reactive group. To form a crosslinked gel by chain-growth polymeriaztion, the macromers, along with any other smaller monomers, in a solution must contain on average more than one reactive group (which may be a covalently reactive group, or a group that binds non-covalently to other macromers). For polymerizations involving step-growth polymerization, the macromers must contain on average more than two reactive groups, and the solution typically contain approximately equal numbers of the two different types of reactive groups. An example of step-growth polymerization is gelation by formation of urethane linkages from the reaction of isocyanate with the hydroxyl groups. For free-radical polymerization of unsaturated materials (chain-growth polymerization), the monomers must contain on average more than one reactive group to crosslink.

The macromers have significant hydrophilic character so as to form water-absorbent gel structures. At least some of the macromers, and preferably most of the macromers, contain hydrophilic domains. A hydrophilic domain in a macromer is a hydrophilic group, block, or region of the macromer that would be water soluble if prepared as an independent molecule rather than being incorporated into the macromer. Hydrophilic groups are required for water dispersibility or solubility, and for retention of water by the gel after gelation, or upon rehydration after drying. The hydrophilic groups of the macromers are preferably made predominantly or entirely of synthetic materials. Synthetic materials of controlled composition and linkages are typically preferred over natural materials due to more consistent degradation and release properties. Examples of useful synthetic materials include those prepared from poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), and poloxamines. Preferably, the water-soluble polymeric blocks are made from poly(ethylene oxide). Preferably, at least 50% of the macromers is formed of synthetic materials.

The hydrophilic groups of the macromers may also be derived from natural materials. Useful natural and modified natural materials include carboxymethyl cellulose, hydroxyalkylated celluloses such as hydroxyethyl cellulose and methylhydroxypropyl cellulose, polypeptides, polynucleotides, polysaccharides or carbohydrates such as Ficoll™ polysucrose, hyaluronic acid and its derivatives, dextran, heparan sulfate, chondroitin sulfate, heparin, or alginate, and proteins such as gelatin, collagen, albumin, or ovalbumin. Preferably the percentage of natural material does not exceed about 50% percent.

The monomers are preferably covalently reactive, and thus form a covalently crosslinked gel. The crosslinked gels are elastic, and further are both elastic and compliant with soft tissue at low polymer concentrations.

Any method of covalent polymerization is potentially useful in the formation of the gels. The reactive groups may include, without limitation, ethylenically unsaturated groups, isocyanates, hydroxyls and other urethane-forming groups, epoxides or oxiranes, sulfhydryls, succinimides, maleimides, amines, thiols, carboxylic acids and activated carboxylgroups, sulfonic acids and phosphate groups. Ethylenically unsaturated groups include acrylates and other unsaturated carboxylic acids, vinylic and allylic groups, cinnamates, and styrenes. Activated carboxyl groups include anhydrides, carbonylimidazoles, succinimides, carbonyl nitrophenols, thioesters, O-acyl ureas, and other conjugated carbonyls. In general, any reactive group that will covalently bond to a second and that can maintain fluidity when exposed to water for enough time to allow deposition and reaction is of use in making a suitable reactive macromer. Due to their excellent stability and slow reactivity in aqueous solutions, ethylenically unsaturated reactive groups are preferred.

The polymerization reaction does not have to result in covalent bonds. A number of materials are known which can form gel structures by changing the ionic conditions of the medium (e.g. alginate) or by changing the temperature of the medium (e.g., agarose, certain poloxamers). Polysaccharides are typical of these materials. Gel-like structures can be formed from proteins, such as gelatin or fibrin. While it maybe more difficult to get these materials to adhere strongly to tissue, they are potentially of use in the hydrogels, particularly as depots for the drug.

Gel formation can be accelerated by inclusion of small (non-macromeric) polymerizable molecules that can assist in linking larger, polymeric macromers. These typically have molecular weights less than about 100 Da, more preferably less than 500 Da. For free radical polymerization, any of the common ethylenically unsaturated molecules can be used. These include derivatives of acrylic and methacrylic acid, such as acrylamide, hydroxyethyl methacrylate (HEMA), and diacrylated or polyacrylated glycols and oligoglycols. Allyl groups (e.g., allyl glycidyl ether) and vinyl groups (e.g., N-vinyl caprolactam and N-vinyl pyrrolidone)

are also of use. Other unsaturated compounds include cinnamic acid and its esters, and maleic, fumaric and itaconic acids and their derivatives.

Similar small molecules can be used to accelerate electrophilic/nucleophilic reactions, such as small polyamines, polyols and polythiols, polyisocyanates, and polysuccimidates.

In the preferred embodiment, the gel is a "FOCAL-GEL™", i.e., a biodegradable, polymerizable macromer having a solubility of at least about 1 g/100 ml in an aqueous solution comprising at least one water soluble region, at least one degradable region which is hydrolyzable under in vivo conditions, and free radical polymerizable end groups having the capacity to form additional covalent bonds resulting in macromer interlinking, wherein the polymerizable end groups are separated from each other by at least one degradable region, as described in U.S. Pat. No. 5,410,016, incorporated herein by reference in its entirety. The individual polymeric blocks can be arranged to form different types of block copolymers, including di-block, tri-block, and multi-block copolymers. The most preferred embodiment is a di-block copolymer including a water-soluble block linked to a biodegradable block, with both ends capped with a polymerizable group, where the biodegradable blocks are a carbonate or hydroxyacid monomer such as a lactide monomer or oligomer.

The biodegradable region is preferably hydrolyzable under in vivo conditions. For example, hydrolyzable group may be polymers and oligomers of glycolide, lactide, ε-caprolactone, other α-hydroxy acids, and other biologically degradable polymers that yield materials that are non-toxic or present as normal metabolites in the body. Preferred poly(α-hydroxy acid)s are poly(glycolic acid), poly(DL-lactic acid) and poly(L-lactic acid). Other useful materials include poly(amino acids), poly(anhydrides), poly(orthoesters), and poly(phosphoesters). Polylactones such as poly (ε-caprolactone), poly(ε-caprolactone), poly(δ-valerolactone) and poly(gamma-butyrolactone), for example, are also useful.

As used herein, a carbonate is a functional group with the structure —O—C(O)—O—. The carbonate starting material can be cyclic, such as trimethylene carbonate (TMC), or can be linear, such as dimethylcarbonate ($CH_3$—O—C(O)—$OCH_3$). After incorporation into the polymerizable macromer, the carbonate will be present at least in part as R—O—C(O)—O—R', where R and R' are other components of the macromer. More preferred carbonates are the cyclic carbonates, which can react with hydroxy-terminated polymers without release of water. Suitable cyclic carbonates include ethylene carbonate (1,3-dioxolan-2-one), propylene carbonate (4-methyl -1,3-dioxolan-2-one), trimethylene carbonate (1,3-dioxan-2-one) and tetramethylene carbonate (1,3-dioxepan-2-one).

In the most preferred embodiments, the macromers contain between about 0.3% and 20% by weight of carbonate residues, more preferably, between about 0.5% and 15% carbonate residues, and most preferably, about 1% to 5% carbonate residues. In those embodiments where hydroxy acid residues are desired, the macromer contains between about 0.1 and 10 residues per residue of carbonate, more preferably between about 0.2 and 5, and most preferably one or more such residue per macromer. In this preferred embodiment, the macromer includes a core of a hydrophilic poly(ethyleneoxide) oligomer (a.k.a. poly(ethyleneglycol) or PEG) with a molecular weight between about 400 and 40,000 Da, most preferably 25,000 Da; an extension on both ends of the core which includes 1 to 10 carbonate residues and optionally between one and five hydroxyacid residues, preferably alpha-hydroxy acid residues, most preferably lactic acid residues, with a molecular weight of bout 50 to 300 Da; wherein the total of all residues in the extensions is sufficiently small to preserve water-solubility of the macromer, being typically less than about 20% of the weight of the macromer, more preferably 10% or less. The ends are capped with ethylenically-unsaturated (i.e., containing carbon-carbon double bonds) caps, with a preferred molecular weight between about 50 and 300 Da, most preferably acrylate groups having a molecular weight of 55 Da. These materials are described in U.S. Pat. No. 6,177,095 to Sawhney, et al. (incorporated herein by reference in its entirety). See also U.S. Pat. No. 5,900,245 to Sawhney, et al. (incorporated herein by reference in its entirety).

The macromers can be synthesized using means well known to those of skill in the art. General synthetic methods are found in the literature, for example in U.S. Pat. No. 5,410,016 to Hubbell et al., U.S. Pat. No. 4,243,775 to Rosensaft et al., and U.S. Pat. No. 4,526,938 to Churchill et al. (incorporated herein by reference in their entirety). For example, a polyethylene glycol backbone can be reacted with trimethylene carbonate (TMC) or a similar carbonate in the presence of a Lewis acid catalyst, such as stannous octoate, to form a TMC-polyethylene glycol terpolymer. The TMC-PEG polymer may optionally be further derivatized with additional degradable groups, such as lactate groups. The terminal hydroxyl groups can then be reacted with acryloyl chloride in the presence of a tertiary amine to end-cap the polymer with acrylate end-groups. Similar coupling chemistry can be employed for macromers containing other water-soluble blocks, biodegradable blocks, and polymerizable groups, particularly those containing hydroxyl groups.

When polyethylene glycol is reacted with TMC and a hydroxy acid in the presence of an acidic catalyst, the reaction can be either simultaneous or sequential. The simultaneous reaction will produce an at least partially random copolymer of the three components. Sequential addition of a hydroxy acid after reaction of the PEG with the TMC will tend to produce an inner copolymer of TMC and one or more PEGs, which will statistically contain more than one PEG residue linked by linkages derived from TMC, with hydroxy acid largely at the ends of the (TMC, PEG) region. When the hydroxy acid contains a secondary hydroxyl, as in lactic acid, then the tendency towards rearrangement is reduced. Upon reaction of, for example, trimethylene carbonate (TMC) with polyethylene glycol (PEG), the TMC linkages in the resulting copolymers have been shown to form end linked species of PEG, resulting in segmented copolymers, i.e. PEG units coupled by one or more adjacent TMC linkages. The length of the TMC segments can vary. Coupling may also be accomplished via the carbonate subunit of TMC. These segmented PEG/TMC copolymers form as a result of transesterification reactions involving the carbonate linkages of the TMC segments during the TMC polymerization process when a PEG diol is used as an initiator. If the product of this first reaction step is then reacted with a reactive end-capping material, such as acryloyl chloride, a significant percentage of the macromer end groups can be PEG hydroxyls, resulting in the attachment of the reactive groups directly to one end of a non-biodegradable PEG molecule. Such a reaction of the PEG/TMC segmented copolymers can be prevented by adding additional segments of other hydrolyzable co-monomers (e.g. lactate, glycolate, 1,4-dioxanone, dioxepanone, caprolactone) on either end of the PEG/TMC segmented copolymer. The basic PEG/TMC segmented copolymer or the further reacted PEG/TMC/ comonomer segmented terpolymer is then further reacted to form crosslinkable macromers by affixing reactive end groups (such as acrylates) to provide a macromer with reactive functionality. Subsequent reaction of the end groups in an aqueous environment results in a bioabsorbable hydrogel.

Polymerization is initiated by any convenient reaction, including photopolymerization, chemical or thermal freeradical polymerization, redox reactions, cationic polymerization, and chemical reaction of active groups (such as isocyanates, for example.) Polymerization is preferably initiated using photoinitiators. Photoinitiators that generate a free radical or a cation on exposure to UV light are well known to those of skill in the art. Free-radicals can also be formed in a relatively mild manner from photon absorption of certain dyes and chemical compounds. The polymerizable groups are preferably polymerizable by free radical polymerization. The preferred polymerizable groups are acrylates, diacrylates, oligoacrylates, methacrylates, dimethacrylates, oligomethacrylates, cinnamates, dicinnamates, oligocinnamates, and other biologically acceptable photopolymerizable groups.

These groups can be polymerized using photoinitiators that generate free radicals upon exposure to light, including UV (ultraviolet) and IR (infrared) light, preferably longwavelength ultraviolet light (LWUV) or visible light. LWUV and visible light are preferred because they cause less damage to tissue and other biological materials than short-wave UV light. Useful photoinitiators are those which can be used to initiate polymerization of the macromers without cytotoxicity and within a short time frame, minutes at most and most preferably seconds. Exposure of dyes, preferably in combination with co-catalysts such as amine, to light, preferably visible or LWUV light, can generate free radicals. Light absorption by the dye causes the dye to assume a triplet state, and the triplet state subsequently reacts with the amine to form a free radical which initiates polymerization, either directly or via a suitable electron transfer reagent or co-catalyst, such as an amine. Polymerization can be initiated by irradiation with light at a wavelength of between about 200–1200 nm, most preferably in the long wavelength ultraviolet range or visible range, 320 nm or higher, and most preferably between about 365 and 550 nm.

Numerous dyes can be used for photopolymerization. Suitable dyes are well known to those of skill in the art. Preferred dyes include erythrosin, phloxime, rose bengal, thionine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst.

Suitable chemical, thermal and redox systems may initiate the polymerization of unsaturated groups by generation of free radicals in the initiator molecules, followed by transfer of these free radicals to the unsaturated groups to initiate a chain reaction. Peroxides and other peroxygen compounds are well known in this regard, and may be considered as chemical or thermal initiators. Azobisbutyronitrile is a chemical initiator. A combination of a transition metal, especially iron, with a peroxygen and preferably a stabilizing agent such as glucuronic acid allows generation of free radicals to initiate polymerization by a cycling redox reaction.

It is also possible to use the macromers with other types of linking reactions. For example, a macromer could be constructed with amine termination, with the amine considered as an active group; and another macromer could be constructed with isocyanate termination, with the isocyanate as the active group. On mixing, the materials will spontaneously react to form a gel. Alternatively, an isocyanateterminated macromer could be polymerized and crosslinked with a mixture of diamines and triamines. Other pairs of reactants include maleimides with amines or sulfhydryls, or oxiranes with amines, sulfhydryls or hydroxyls.

The copolymers and macromers can have tailorable solubility and solution viscosity properties. The hydrogels can have tailorable modulus and degradation rate. For a given solution concentration in water, the viscosity is affected by the degree of end linking, the length of the TMC (and other hydrophobic species) segments, and the molecular weight of the starting PEG. The modulus of the hydrogel is affected by the molecular weight between crosslinks. The hydrogel degradation rate can be modified by adding a second, more easily hydrolyzed comonomer (e.g. lactate, glycolate, 1,4-dioxanone) as a segment on the ends of the basic PAG/TMC copolymer prior to adding the crosslinkable end group to form the macromer.

In some cases it is desirable to increase the viscosity of the macromer solution at the time of application to the tissue so that the macromer remains more firmly at the site of application. Polymers which can be used to increase the viscosity of the macromer solution include: glycosaminoglycans (GAG) such as hyaluronic acid (HA), carboxymethyl cellulose (CMC), dextran, dextran sulfate, and polyvinylpyrolidone (PVP). These are typically added to the macromer solution immediately before application to the tissue.

As used herein, a "biodegradable" material is one that decomposes under normal in vivo physiological conditions into components that can be metabolized or excreted. Functional groups having degradable or resorbable linkages are incorporated into the structure of the hydrogel matrix to provide for its resorption over time. These functional groups may be incorporated within the macromers to form part of the backbone of the polymer strands of the hydrogel or as crosslinks between the polymer strands. Examples of degradable units may include, but are not limited to, esters, carbonates, carbamates and the like.

The length of time it takes for the hydrogel to biodegrade may be tailored to provide a hydrogel that persists long enough to generate the required tissue level of the drug through the critical period, which extends from about the second postoperative day to about the seventh postoperative day, or preferably from about the first or second postoperative day to about the tenth or fourteenth. Given the achievement of this objective, shorter degradation or resorption times such as less than about three months are generally preferred. Degradation or resorption times less than about fifteen days are particularly preferred.

As used herein, a "biocompatible" material is one that stimulates only a mild, often transient, implantation response, as opposed to a severe or escalating response. Biocompatibility may be determined by histological examination of the implant site at various times after implantation. One sign of poor biocompatibility can be a severe, chronic, unresolved phagocytic response at the site. Another sign of poor biocompatibility can be necrosis or regression of tissue at the site. In the preferred embodiment, a biocompatible material elicits a minimal or no fibrosis or inflammation. This can be achieved through selection of hydrogel composition, and particularly through the use of hydrogel components resulting in degradation of the hydrogel in vivo in less than about two weeks, more preferably within seven to ten days.

A material is tissue adherent if it requires a force to remove the material from the tissue. Thus, the general and practically useful measurement of adherence is that the gel, when applied to the tissue, remains attached to the tissue for at least as long as is required to obtain the therapeutic effect of the drug. Typically, this time period will be sufficiently long to observe at least about 10% elution of the drug, and preferably 20% elution or more, before detachment or degradation of the gel.

Ex vivo tests can be used to determine a material's potential adherence. In evaluating potential adherence of materials, it is useful to have an in vitro test to determine formulations that are likely to have the desired degree of adherence to the tissue surface. One method of judging adherence is to require that upon a gradual increase in a detaching force, the force required to remove the gel from the tissue is greater than or approximately equal to the force required to cause cohesive failure of the gel (or the tissue, if lesser). Thus on attempting to remove the material, either the material or the tissue experiences cohesive failure at a lesser force than, or at approximately the same force as, the force at which the bond between the material and the tissue experiences adhesive failure. Materials that require a force of about 20 dynes/cm$^2$ to remove them from the tissue are sufficiently adhesive for delivery of anti-arrhythmic agents.

Adherence can be described qualitatively as "excellent", when cohesive failure is required for removal from the surface, "good" when failure is partially cohesive and partially adhesive, "fair" when removal requires only adhesive failure (i.e., detachment of the gel from the surface) and more than 20 dynes/cm$^2$ of force is required to produce adhesive failure, and "poor" if none of these criteria are satisfied. Force can be measured using a mechanical properties tester, such as an Instron™ tester or other device.

In vitro adherence that is "good", "excellent", or, in many cases, "fair", has generally been observed to be sufficient for in vivo use. However, these in vitro measurements are for convenience, and the formulation may need to be optimized based on in vivo release of drug before detachment.

The hydrogels are preferably highly compliant with the tissue to which they adhere. Thus, the gels stretch and bend along with the tissue. Cardiac tissue is in continual motion, and the hydrogel should not significantly disturb this motion. It is preferable that the response to stress within these limits be substantially elastic, i.e., reversible. Thus the hydrogel should remain as a coherent material for at least the period required for delivery of the anti-arrhythmic agent.

In a preferred embodiment, the hydrogel composition is selected to provide acceptable levels of fibrosis or tissue reaction. This can be achieved through the selection of the reactive formulation, and other techniques known to those skilled in the art in drug delivery utilizing polymeric delivery devices.

B. Anti-arrhythmic Agents

Anti-arrhythmic agents are used for the treatment or prevention of cardiac arrhythmias. They may affect the polarization-repolarization phase of the action potential, its excitability or refractoriness, or impulse conduction or membrane responsiveness within cardiac fibers. A modification of the classification system proposed by Vaughan-Williams is a frequently used classification system for anti-arrhythmic agents. This classification system is based in part on the ability of anti-arrhythmic agents to modify the cardiac cellular excitatory currents ($Na^+$ or $Ca^{2+}$), action potential duration and automaticity. These effects of the agents on isolated cardiac cells are believed to be responsible for some of the anti-arrhythmic properties of the agents. (See *Harrison's Principles of Internal Medicine* (13$^{th}$ Ed.), p. 1032–1034 (McGraw-Hill Inc. 1994) for additional information.)

Anti-arrhythmia agents are often organized into four main groups according to their mechanism of action: type I, sodium channel blockade; type II, beta-adrenergic blockade; type III, repolarization prolongation; and type IV, calcium channel blockade. Type I anti-arrhythmic agents include lidocaine, moricizine, mexiletine, tocainide, procainamide, encainide, flecanide, tocainide, phenytoin, propafenone, quinidine, disopyramide, and flecainide. Type II anti-arrhythmic agents include propranolol and esmolol. Type III includes agents that act by prolonging the duration of the action potential, such as amiodarone, artilide, bretylium, clofilium, isobutilide, sotalol, azimilide, dofetilide, dronedarone, ersentilide, ibutilide, tedisamil, and trecetilide. Type IV anti-arrhythmic agents include verapamil, diltaizem, digitalis, adenosine, nickel chloride, and magnesium ions.

The preferred anti-arrhythmic agents are poorly soluble in water (i.e. hydrophobic). In terms of the solubility classification of the United States Pharmacopoeia (USP 24/NF 19, effective Jan. 1, 2000; p. 2254), the preferred solubility classes are: "slightly soluble", requiring 100 to 1000 parts of solvent to dissolve; "very slightly soluble", requiring 1000 to 10,000 parts of solvent; and "practically insoluble, or insoluble", requiring over 10,000 parts of solvent. Collectively, these classes are defined herein as "poorly soluble". Of the various classes of anti-arrhythmic agents, type III are preferred. Of these, amiodarone, dronedarone and sotalol are preferred, and amiodarone is the most preferred anti-arrhythmic agent for delivery in a hydrogel. Dronedarone is similar to amiodarone and is believed to be at least as insoluble in water.

Amiodarone hydrochloride (amiodarone) is an approved class III anti-arrhythmic drug. Amiodarone is a potassium channel blocker that prolongs the action potential duration and refractory period of all cardiac fibers. (See *Dorland's Illustrated Medical Dictionary* 28$^{th}$ ed. (W.B. Saunders Co. 1994)) Amiodarone is typically administered orally in multiple doses over an extended period of time to reduce the risk of atrial fibrillation. It has a reduced clearance rate and a very long half-life, and is associated with numerous side effects at the conventional therapeutic dose. Amiodarone applied in a single application directly to the heart is expected to be similarly effective, with a potential reduction in side effects because a lower required dose is anticipated.

C. Formulations

The slow dissolution rate for poorly soluble anti-arrhythmic agents controls their rate of efflux from the gel. The rate of efflux for such anti-arrhythmic agents can also be controlled by selecting the particle size of the drug particles that are suspended in the macromer solution before its polymerization. Particles of a particular size can be made by any known method, including grinding, milling, cryofracture, precipitation, spraying, spray drying, and/or classification. Dispersion and stabilization of the particles within the macromer solution may be achieved with the use of surfactants such as, but not limited to, PLURONIC.

It has been discovered, as demonstrated in Example 3, that a precipitated nanoparticle form is the preferred formulation for amiodarone. This fine precipitate can be readily and reproducibly achieved by dilution of a stable aqueous solution of amiodarone with an aqueous solution of synthetic hydrogel-forming polymers. Surfactants and alcohols are used to make amiodarone soluble in the aqueous solution.

In the amphiphilic macromers used in the Examples, the hydrophobic groups form micelles in aqueous solution. These micelles may act as nucleation sites during the precipitation of amiodarone and then serve to prevent coalescence of the precipitate. If this is correct, the particle size of the drug can be controlled by varying the concentration of nucleation sites. Fewer nucleation sites per unit volume would lead to fewer but larger particles, which could slow the rate of delivery of the anti-arrhythmic agent.

More soluble anti-arrhythmic agents can also be used, but their efflux rate from the gel usually must be altered to achieve the necessary delivery rate. Such soluble anti-arrhythmic agents include those falling in United States Pharmacopoeia classes "very soluble", "freely soluble", "soluble", and "sparingly soluble". Typical means of altering release rates include encapsulating the agents in micro particles or liposomes and conjugating the agents to macromolecules. They can be made less soluble by altering the salt or using the free acid/base form of the agents.

Pre-encapsulation is used for the small, water-soluble drugs (typically of molecular weights less than 1000 Da) that are incorporated into hydrogels, to decrease the rate of release of these drugs. The encapsulation may be by any conventional means. One means is entrapment in micro particles of a degradable, water-insoluble polymer. Typical materials are polymers and copolymers of lactic acid, glycolic acid, and copolymers thereof (e.g., PLGA). Other materials used to form suitable micro particles are copolymers of ethylene and vinyl acetate (EVAC) and polymers of anhydrides, such as poly sebacic anhydride. Particles of drug may also be pre-encapsulated with polymers such as EVAC and PLGA, or with thin layers of materials that dissolve in vivo, for example, the enteric coatings or other coatings typically used for oral delivery, such as gelatin.

Release of more soluble anti-arrhythmic agents can be slowed by conjugating small molecules to polymers by degradable or reversible linkages. Many such systems are described in the art. In one embodiment, such systems are generated by immobilizing a binding or targeting molecule for the drug, such as an antibody or lectin, which is saturated with the drug, in the gel. In another typical embodiment, drug is attached to a polymer bearing reactive groups, such as to the hydroxyl of polyvinyl alcohol, to a carboxyl, sulfonate or amine group of a polysaccharide or the hydroxyl or carboxyl of an alpha-hydroxy acid (e.g., lactic or glycolic acid), or to a carboxylic group on a polymer (e.g., alginate, polyacrylic acid) via an anhydride, an ester, a carbonate, or carbamate linkage. Many similar methods are described in the art.

The solubility of some drugs, particularly amines, can be decreased by preparing them in their neutral ("free base") form. Such drugs often can also be administered as suspensions in oil, which in turn is dispersed in water, usually with surfactant stabilizers.

D. Levels of Drug Loading

The level of loading of the drug in the gel-forming solution will normally be as high as practical, while leaving a margin of loading to prevent premature precipitation or aggregation, or inhibition of gel formation. The level obtainable will depend on the drug; on the type of encapsulant, if present; and on the properties of the gel. The macromer solution is preferably between 3 and 20% by weight FOCALSEAL™, with 5 to 7% being most preferred. The amiodarone concentration used in the examples is typically between 0.5 and 1% by weight, but this will depend in part upon the source and form of the amiodarone. Gel polymerization rate and final gel may be significantly affected by drug concentration. Use of other macromers affects the optimal level. Fortunately, acceptable loading ranges are easily determined for a particular system by varying the loading and determining the properties of the formed gel.

II. Methods of Forming the Hydrogels

It is important to provide a way for the physician to deliver a well-defined amount of the AAR, so that the therapeutic effect can be obtained. In one method, the anti-arrhythmic agent is provided in a formulation that forms a hydrogel in vivo. In a second method, the anti-arrhythmic agent is provided to the patient in a preformed hydrogel "patch".

As noted above, the gels are formed by a polymerization reaction, which may be any reaction that can be carried out in a substantially aqueous environment and is not damaging to tissue. The gels may be polymerized in vivo or in vitro.

As discussed above, adherence of gels to tissue can be optimized by techniques that employ functional primers, as described in U.S. Pat. No. 5,800,373 to Melanson et al., U.S. Pat. Nos. 5,844,016, or 5,900,245 to Sawhney et al. for gels formed by polymerization of ethylenically unsaturated precursors. Suitable gel compositions form strong bonds to tissue. These techniques are also applicable to creating strong adherence of the materials to tissue, including tissue to which it is difficult to obtain adherence by conventional methods, for example, cartilage.

A general procedure for applying materials to the tissue involves brushing or dabbing primer over a larger area than that over which the material is applied. Thereafter, material is brushed or dabbed over the deposited primer. Then bulk material is applied by dripping (if liquid) or spreading (if paste) over yet a smaller area of the treated zone. Then light (at appropriate wavelength, intensity, distance and for an appropriate time) is applied at each zone, or other means of polymerizing the material are used.

A. In Vivo Polymerization

In this embodiment, the drug is formulated in appropriate excipients (if any) in a vial, and is taken up in a known amount of hydrogel forming material. This solution is applied to the tissue, and polymerization is effected to form a gel adherent to the tissue.

In the preferred embodiment, the solution is polymerized by illumination of a photoinitiator or photosensitizer in the solution. In this case, the mixing of two solutions at the time of application will not necessarily form a gel; however once the solutions are illuminated by light of an appropriate frequency, a gel will form, as described in U.S. Pat. No. 5,410,016 to Hubbell et al. incorporated herein by reference in its entirety.

In vivo polymerization has the advantage of being able to produce "good" to "excellent" adherence when polymerized on the tissue surface (as defined in Table 1). This is particularly true when the tissue is first primed or otherwise pretreated with an agent (primer) stimulating polymerization (as known to those skilled in the art, for example, as described in U.S. Pat. No. 5,844,016 to Sawhney et al. and U.S. Pat. No. 5,834,274 to Hubbell et al. incorporated herein by reference in their entirety) prior to the application of the macromer composition containing the anti-arrhythmic drug. See also U.S. Pat. Nos. 5,567,435; 5,844,016; 5,986,043;

6,060,582; and 6,306,922 incorporated herein by reference in their entirety. In these methods, an aqueous solution containing a photoinitiation system, including one or more photoinitiators, photosensitizers and co-initiators, amine or amide electron transfer agent, redox accelerant system for the photoinitiation system (such as a metal ion and a peroxide); and a photopolymerizable macromer solution, are applied to the tissue, and the solution is polymerized by exposure to UV or visible light at room or body temperature.

B. In Vitro Polymerization

In a second embodiment, hydrogel patches containing anti-arrhythmic drugs are polymerized in vitro and then adhered to the tissue surface. The drug in any of the above formulations can be entrapped in a hydrogel in vitro, which is optionally preserved by freezing or drying, and is subsequently transferred to the cardiac tissue. The preformed gel patch, or more than one preformed gel patch, is then adhered to the cardiac tissue. Adhesion of the patch may be achieved by the polymerization of a hydrogel-forming material, which may be the same as or different from the material used to form the gel patch, placed between the preformed gel patch and the tissue, or optionally encapsulates the entire pre-formed gel. Adhesion may also be achieved by completing polymerization of a partially polymerized gel patch onto the tissue. A partially polymerized gel patch is prepared by reducing time exposure to polymerization conditions or by quenching polymerization.

In vitro polymerization has the advantage of providing a reliable means of delivering a precisely defined dose of the drug. The preformed gels should have the same properties as gels formed in vivo.

This method of application may be regarded as another form of application of an encapsulated drug to the tissue, since the adhesion to the tissue is provided by a hydrogel that is formed in situ on the tissue. The preferred method of attaching the gels to the tissue surface is to use macromer solutions to adhere the preformed gel to the tissue. Adherence is also preferably in the "good" to "excellent" range (see Table 1).

Techniques for producing strong adherence of the gel to the tissue include applying an initiator or promoter of polymerization to the tissue at the site; applying a thin layer of gelling solution having a high concentration of a polymerizable reagent at the site; applying materials bearing one half of a reactive pair to the site, optionally a member of a reactive pair which is also reactive with tissue; and applying mechanical action to a layer of polymerizable material on the tissue (before polymerization) to ensure that no layer of fluid, such as mucus or the like, separates the polymerizable material from the tissue.

III. Methods of Using the Hydrogels

Any medical treatment that exposes or disturbs the heart has the potential to stimulate arrhythmias. Open heart operations are prominent among these treatments, including particularly cardiac bypass surgery and valve replacement. Other treatments that may benefit from application of anti-arrhythmic agents include implantation of pacemakers and pacemaker leads, cardiac reduction surgery, aneurysm repair, and angioplasty, stenting, and other endovascular treatments for coronary obstruction.

The conventional mode of administration of anti-arrhythmic agents is oral or intravascular, resulting in systemic delivery. Typically, in systemic delivery, a larger initial dose is given, and then a smaller maintenance level is continued for several days or up to a week. Some studies indicate that the period of highest risk of arrhythmia is about four to seven days after surgery. Kinetics of build-up in the cardiac tissue are complex, in part because of the poor solubility of some anti-arrhythmic drugs and their accumulation into fatty tissue, such as amiodarone.

However, as described herein, the gel can be applied at the time of surgery and the drug delivered directly to the affected cardiac tissue. This simplifies the kinetics of penetration of the drug into the tissue. When polymerized in situ, the gel can be applied in open surgery by any method. In endoscopic surgery, it is preferably brushed or sprayed onto the tissue surface using a device designed for percutaneous use, but may be dripped from a mixing apparatus. When used to treat the inside of vessels, catheters such as those described in U.S. Pat. No. 5,947,977 to Slepian et al. or U.S. Pat. No. 5,779,673 to Roth et al. can be used to apply the gel.

The dosage of anti-arrhythmic drugs for use in a human or animal and its minimum duration can be determined with only routine experimentation in view of the animal studies presented in the examples below and the known drug kinetics, including half-life, solubility and other readily ascertainable properties. The effective dosage can be determined from tissue concentrations and physiological effects over time in cardiac tissue of animals, after application of a known concentration of the drug in the hydrogel. For example, it has been found that administration of about 1.5 mg of amiodarone to rabbit heart, in essentially the formulation described in Example 1 below, produced a tissue loading at seven days of about 20 to 40 micrograms per gram of tissue, which is believed to be in the therapeutic range. Such animal studies are routine in determining dosage for any drug. The dosage of the drug will also be optimized based on the period of time over which delivery is to be obtained and the release rate from the hydrogel as well as the degradation characteristics of the hydrogel, to deliver a dosage effective to lengthen the atrial effective refractory period (AERP) in the heart tissue.

Amiodarone

In the particular case of amiodarone, its insolubility means that it is relatively slow to equilibrate in the cardiac tissue and relatively slow to diffuse out once administration is discontinued. Because of these considerations, the duration of delivery of amiodarone should be at least one day. Delivery beyond about two weeks is unlikely to significantly improve the therapeutic outcome. A preferred delivery period is over a postoperative period ranging from about two days to about fourteen days, and more preferably from about four days to about seven days.

Delivery over shorter or longer periods is acceptable provided that the tissue level of amiodarone is maintained at a physiologically effective level for at least about two or three days postoperatively and preferably extending through at least seven days and more preferably at least ten days. An effective tissue level of amiodarone is preferably achieved within about one day post-operatively, or within at most two or three days.

The present invention will be further understood by reference to the following non-limiting examples.

The Following Materials are Used in the Examples:

PEG-based reactive macromers were used in all of the studies. These materials are available from Genzyme Biosurgery, One Kendall Square, Cambridge, Mass. 02139, under the trademark "FOCALSEAL™". There are three forms: FOCALSEAL™-S, FOCALSEAL™-L, and FOCALSEAL™-M. All consist of a core of PEG, partially concatenated with monomers which are linked by hydrolyzable (biodegradable) linkages, and capped at each end with a photopolymerizable acrylate group. These differ based on the molecular weight of the core PEG, the number of PEG molecules, and the number and composition of the biodegradable monomers. FOCALSEAL™-S includes PEG with molecular weight 19,400±4000 Daltons; FOCALSEAL™-L and FOCALSEAL™-M include PEG with molecular weight 35,000±5000 Daltons. FOCALSEAL™-S includes trimethylene carbonate ("TMC") monomers in a ratio of at least six or seven TMC molecules to each PEG, typically twelve to thirteen TMC molecules to each PEG, and lactide monomers, typically four lactide molecules to each PEG molecule, with a maximum of five lactide monomers to each PEG. FOCALSEAL™-M is the same as FOCALSEAL™-S with the exception of the molecular weight of the PEG. FOCALSEAL™-L includes TMC molecules in a ratio of less than ten, more typically seven, TMC molecules to each PEG. U.S. Pat. No. 6,083,524 describes the synthesis in detail of these materials.

These materials are polymerized by preparing a solution containing a photoinitiator system. For example, a 10 g aqueous formulation consists of 1 g FOCALSEAL™-S, 54 mg triethanoloamine (TEOA), 80 mg mono-potassium phosphate (KPhos) (1.2% by weight or 19 mM), 40 mg vinylcaprolactam (VC) (0.5% by weight), and 0.4 mg of Eosin-Y (10–100 ppm, preferably 30–60 ppm). Surfactant is preferably added, such as PLURONIC™ F127, to 0–1% by weight, most preferably 0.25% by weight. t-Butylperoxide is then added to a concentration of typically 0.0125% by weight. Ferrous gluconate (Fe-Gluconate) may also be added.

EXAMPLE 1

Preparation of Amiodarone-loaded FOCALSEAL-L™ Hydrogel Patches Directly onto Tissue for Release of CORDARONE™

CORDARONE™ (Wyeth Laboratories Inc., Philadelphia, Pa.) (0.5 g) was added to FOCALSEAL-L™ macromer solution (Genzyme Corporation, Cambridge, Mass.) (4.5 mL) and the combination was mixed with a spatula until homogeneous. Over time, the material showed phase separation, which resulted from the precipitation of amiodarone from the macromer solution, and the material formed a submicron amiodarone suspension.

The resulting amiodarone suspension was applied to the myocardium of a live pig by brushing the FOCALSEAL-L™ primer solution onto the myocardium, mixing a small volume of the FOCALSEAL-L™ macromer component containing amiodarone with the primer, and overlaying the mixture with a larger volume of macromer component containing amiodarone. The material was then illuminated with 40 seconds of visible light to polymerize the macromer and form a hydrogel patch onto the tissue. The preparation and use of the FOCALSEAL-L™ hydrogel is described in more detail in the Instructions for Use and in U.S. Pat. No. 6,121,341 to Sawhney et al.

The adherence of the hydrogel patch was scored 20 minutes following administration to the heart. The method of adherence scoring is detailed in Table 1 below. The scale ranges from 0 to 4, with the numbers at the lower end of the scale indicating that the gel was more easily removed, and the numbers at the higher end of the scale indicating that more force was needed to remove the hydrogel patch. The hydrogel patches showed good adherence on the porcine myocardium, with adherence scores ranging between 3 to 4.

TABLE 1

Adherence Scoring For Gel Patches On Tissue

| Adherence Score | Decision Criteria |
| --- | --- |
| 0 | Gel patch falls off when touched or has fallen off during test. |
| 1 | The entire piece of gel patch can be removed by lifting one end of the gel patch. |
| 2 | Peeling motion is required to remove the gel patch. |
| 3 | Scraping is required to remove the gel patch. |
| 4 | Vigorous, repeated scraping is required to remove the gel patch. Gel patch can only be removed in pieces. |

EXAMPLE 2

Amiodarone in a Solid Particulate Form in FOCALSEAL-L™

Amiodarone (Isochem, SNPE North America, Princeton, N.J.) (11 g) was added to a solution of distilled water containing 0.3125% PLURONIC™ F127 as surfactant (600 g). The particles were mixed to form a coarse suspension using a Caframo overhead mixer at 500 rpm for 5 minutes. Once the particles were completely wetted with the aqueous surfactant solution, the mixture was transferred to a microfluidizer (Microfluidics International Corp., Newton, Mass.) and homogenized at 20,000 psi for 15 minutes.

The fine suspension was transferred to a 2 L flask and assayed for drug content by HPLC. Based on the assay results, the drug concentration was adjusted to 1.43% by adding a solution of 0.25% PLURONIC™ F127 in distilled water. The solution was mixed well and part of the solution (700 g) was transferred to a 2 L beaker. The FOCALSEAL-L™ macromer (200 g) was added to the beaker and mixed until dissolved. A buffer containing 10x the buffer formulation components was added to the solution (95 g) and mixed for 30 minutes. Vinyl caprolactam (5 g) was added to the solution and mixed for an additional 30 minutes. The resulting suspension of amiodarone in FOCALSEAL-L™ macromer was transferred into syringes and frozen at −40° C. prior to use.

An adherence testing scheme that is similar to the one described in Example 1 was performed.

The solid particulate form in FOCALSEAL-L™ gels received adherence scores that were similar to the adherence scores of the CORDARONE™-loaded macromer formulation.

EXAMPLE 3

Release Rate of Amiodarone from Hydrogels

Three different particle sizes of amiodarone were tested to determine the effect of particle size on release rate from hydrogels. Amiodarone was obtained from three different suppliers. Amiodarone purchased from a first supplier (Sigma) was determined to have a mean particle size of 25 microns by particle size analysis using a Malvern Mastersizer 2000. Amiodarone from a second supplier (Isochem) had a particle size of 19 microns. A third particle size was obtained by mixing CORDARONE™ brand amiodarone with a hydrogel forming solution, as described in Example 1. The CORDARONE™ material is an injectable solution of amiodarone in water containing TWEEN™ surfactant and benzyl alcohol. Upon mixing with the gel-forming solution, the amiodarone precipitated, forming a hazy suspension of non-settling particles. Microscopic examination indicated that these particles were submicron in size. Amiodarone from the other two suppliers was prepared in gels according to the procedure described in Example 2. The gel forming solution for all three types of amiodarone was FOCALSEAL-L™ macromer.

After mixing amiodarone into the gel forming solutions, gel patches in the shape of disks were formed by polymerizing 0.5 mL of the formulation in a 1 cm diameter TEFLON™ fluorocarbon mold with visible light. Gel disks were placed in a flow-through dissolution apparatus and sampled over time. Drug release kinetics were determined by measuring the residual drug in the gel disks as a function of time.

The elution curves of amiodarone are shown in FIG. 1. It can be seen that the efflux of amiodarone was slowest from the larger solid particles (i.e. Sigma particles of 25 microns), faster from the smaller solid particles (i.e. Isochem Particles of 19 microns), and fastest from the submicron precipitate (i.e. CORDARONE™ particles of less than 1 micron). Thus, even neglecting the possible influence of the excipients introduced with the CORDARONE™ preparation, the efflux rate of the poorly soluble amiodarone is controllable by selection of the particle size. Moreover, appropriate efflux rates for cardiac tissue treatment may be obtained by this means.

EXAMPLE 4

Effect of CORDARONE™ Addition on Modulus and pH of FOCALSEAL-L™ Patches

This study was to evaluate the change in gel patch stiffness and formulation pH following dilution of the hydrogel with 0 to 20% (w/w) CORDARONE™ (0 to 20% weight amiodarone/weight of hydrogel). This formulation would have the advantage of using off-the-shelf commercial products and allow operating room mix-in.

FOCALSEAL-L™ was prepared by adding known volumes of FOCALSEAL-L™ to CORDARONE™ to achieve 0 to 20% CORDARONE™ loading.

Figure 2A:
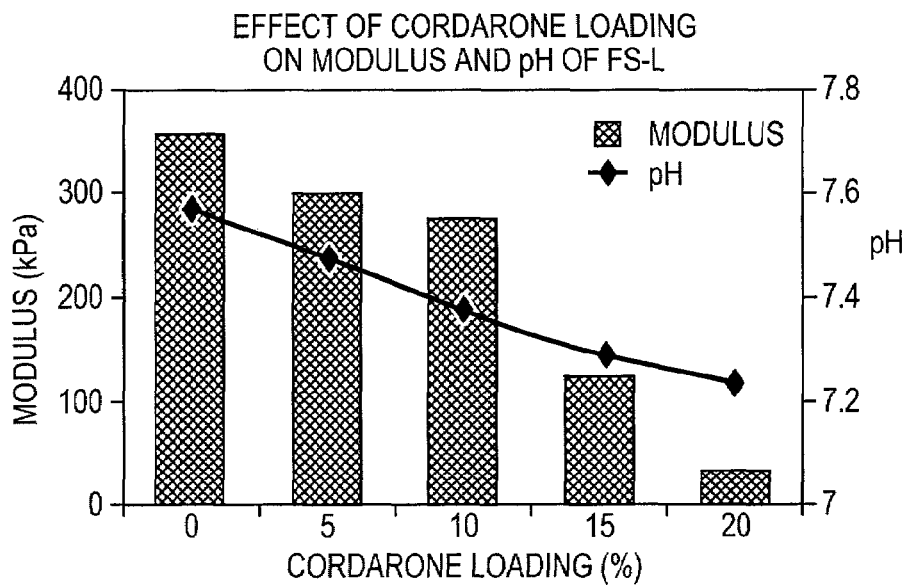
FIG. 2A is a graph of modulus (kPa) and pH of FOCALSEAL-L® hydrogels formed with increasing concentrations of CORDARONE, up to 20% loading of the hydrogel.

The graph shown in FIG. 2A demonstrates a decrease in pH and modulus as CORDARONE concentration is increased. CORDARONE can be loaded into the FOCALSEAL-L formulation at levels up to 15% and maintain acceptable pH and modulus values.

EXAMPLE 5

Effect of Amiodarone (Particulate Form) Addition on Modulus and pH of FOCALSEAL-L™

This experiment was conducted to evaluate the change in gel stiffness and formulation pH following addition of 0 to 10% amiodarone particles to the macromer solution which was then polymerized to form hydrogel. This formulation would be prepared as a suspension of amiodarone particles in a frozen FOCALSEA-L™ syringe.

FOCALSEAL-L™ was prepared by dispersing known amounts of amiodarone (particulate form) in a surfactant solution, then adding the appropriate FOCALSEAL formulation components that resulted in final amiodarone concentrations between 0 and 10%. The solution was mixed for 3 hours prior to pH and modulus measurements.

Figure 2B:
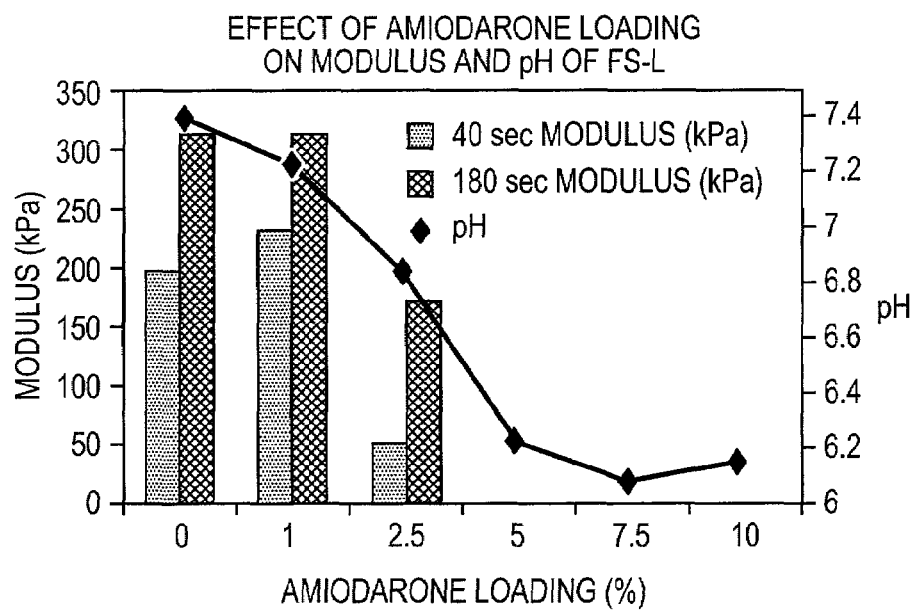
FIG. 2B is a graph of modulus (kPa) and pH as a function of amiodarone loading up to 10% of the FOCALSEAL-L® hydrogel.
Figure 3:
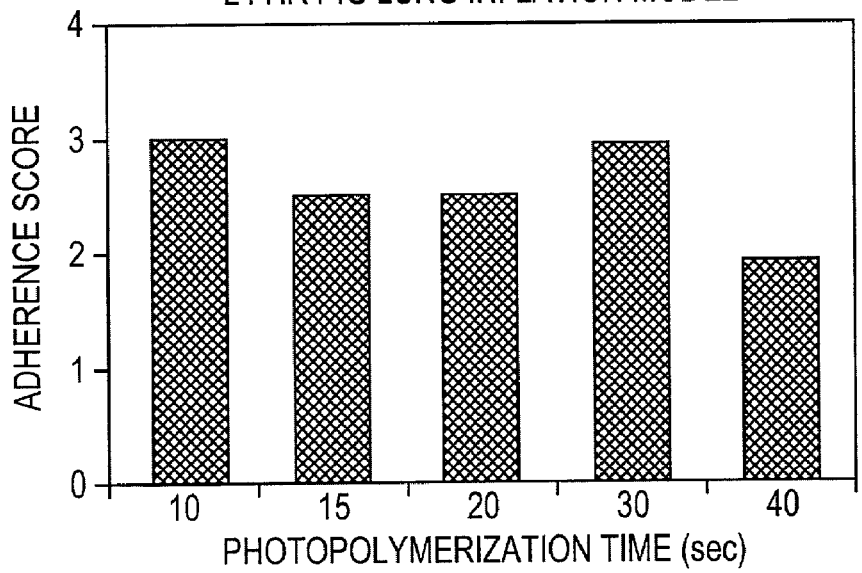
FIG. 3 is a graph of adherence scores for FOCALSEAL-L® hydrogel patches polymerized in vitro, then applied to pig lung tissue, as a function of the polymerization time in seconds, up to 40 seconds.

The graph shown in FIG. 2B demonstrates a decrease in pH and modulus as amiodarone concentration (particulate form) is increased. Amiodarone can be loaded into the FOCALSEAL-L™ formulation at levels to about 1.5% and maintain acceptable pH and modulus values.

EXAMPLE 6

Adherence Testing of In Vitro Polymerized FOCALSEAL-L™ Hydrogels Patches Using the Pig Lung Inflation Model This experiment was conducted to evaluate over 24 hour the adherence of FOCALSEAL-L™ hydrogel patches prepared by applying a preformed hydrogel polymerized in vitro in the shape of a disk onto an inflating, explanted pig lung.

FOCALSEAL-L™ hydrogel disks were prepared by placing 0.5 mL of macromer solution into a convex mold and illuminating the macromer from between 10 to 40 seconds. To apply the disks to the pig lung, the lung was brushed with FOCALSEAL™ primer and a drop of FOCALSEAL™ macromer was applied to the underside of the disk. The disk was then placed on the primed tissue and then crosslinked by iron-redox and photopolymerization chemistries. The lung was attached to an inflation/deflation apparatus for 24 hours. The disks were then evaluated for their relative tissue adherence using the Adherence Scoring Scale detailed in Example 1.

EXAMPLE 7

Evaluation of FOCALSEAL-S® Macromer with Amiodarone (1% and 4%) on Porcine Cardiac Tissue This study was conducted to evaluate and measure after 7 days the amount of amiodarone delivered from the hydrogel patches into cardiac tissue using FOCALSEAL-S® macromer solutions (obtained from Genzyme) loaded with 1% and 4% amiodarone deposited and polymerized in vivo on a beating porcine heart.

Treatment Schedule:

| Group | Carrier | Drug loading | Sites per Pig |
| --- | --- | --- | --- |
| Group 1 | FOCALSEAL-S ® macromer | Control 0% | 2 |
| Group 2 | FOCALSEAL-S ® macromer | 1% amiodarone | 2 |
| Group 3 | FOCALSEAL-S ® macromer | 4% amiodarone | 2 |

Table 2 shows the individual and average volumes of macromer solution applied to pig atria and ventricles. The volumes of drug loaded macromer solution were 0.5±0.1 mL.

TABLE 2

Macromer Solution Volumes Applied to Pig Atria and Ventricles

| PIG # | MACROMER SOLUTION | ATRIUM (ML) | VENTRICLE (ML) |
| --- | --- | --- | --- |
| 1 | CONTROL (GEL ONLY) | 0.6 | 0.4 |
|  | 1% AMIODARONE | 0.6 | 0.4 |
|  | 4% AMIODARONE | 0.5 | 0.6 |
|  | Average ± SD | 0.6 ± 0.1 | 0.5 ± 0.1 |

TABLE 2-continued

Macromer Solution Volumes Applied to Pig Atria and Ventricles

| PIG # | MACROMER SOLUTION | ATRIUM (ML) | VENTRICLE (ML) |
|---|---|---|---|
| 2 | CONTROL (GEL ONLY) | 0.5 | 0.5 |
|   | 1% AMIODARONE | 0.6 | 0.4 |
|   | 4% AMIODARONE | 0.6 | 0.6 |
|   | Average ± SD | 0.6 ± 0.1 | 0.5 ± 0.1 |

Hydrogel Drug Extraction Results:

Table 3 shows the individual amounts of amiodarone released from 1% and 4% amiodarone-loaded gels, respectively. The 1% and 4% amiodarone-loaded gel patches released on average 39±9% and 19±3% of the drug, respectively.

TABLE 3

Amiodarone Released from 1% and 4% Drug-loaded FOCALSEAL-S ® Gels

| PIG # | SAMPLE | % AMIODARONE RELEASED |
|---|---|---|
| 1 | 1% Atrium gel | 35.6 |
|   | 4% Atrium gel | 20.6 |
|   | 1% Ventricle gel | 26.8 |
|   | 4% Ventricle gel | 18.5 |
| 2 | 1% Atrium gel | 36.6 |
|   | 4% Atrium gel | 23.6 |
|   | 1% Ventricle gel | 53.3 |
|   | 4% Ventricle gel | 20.1 |

Figure 4:
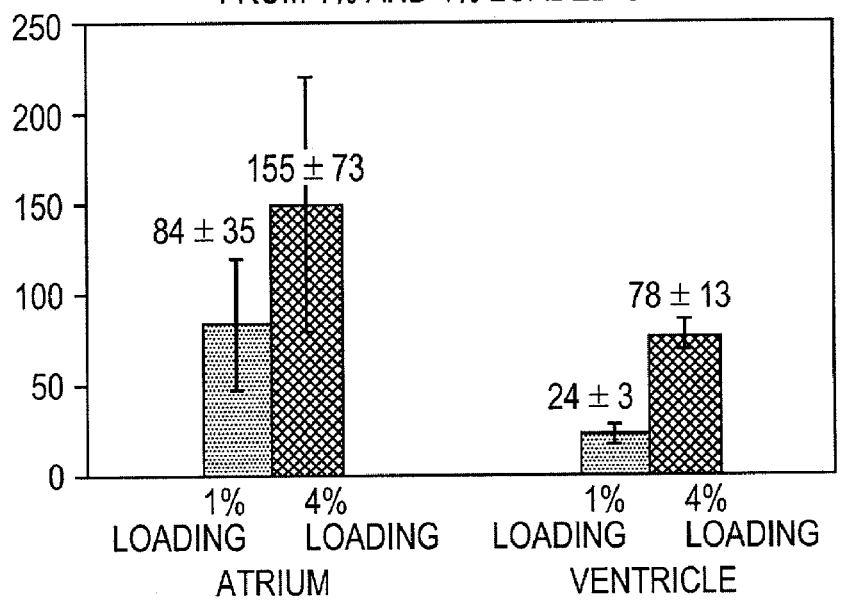
FIG. 4 is a graph of average amiodarone concentrations in porcine atrial and ventricular tissue following delivery to the tissue from 1% and 4% loaded FOCALSEAL-S® hydrogels for a period of seven days.

Tissue Analysis—Drug Content:

Table 4 and FIG. 4 show the tissue levels of amiodarone following delivery for seven days from 1% and 4% loaded FOCALSEAL-S® hydrogel patches.

Atrial tissue under 1% and 4% gels had average amiodarone concentrations of 84±35 µg/g tissue and 155±73 µg/g tissue, respectively. Ventricle tissue under 1% and 4% gel patches showed average amiodarone concentrations of 24±3 µg/g tissue and 78±13 µg/g tissue, respectively. Lung tissue adjacent to gel-treated sites showed amiodarone levels not exceeding 17 µg/g tissue.

TABLE 4

Amiodarone Tissue Concentrations under Control and Drug loaded FOCALSEAL-S

| | [Amiodarone] (µg/g tissue) | |
|---|---|---|
| Tissue Sample | Pig #1 | Pig #2 |
| Rt. Atrium-control gel | 0 ± 0 | 0 ± 0 |
| Rt. Atrium-1% gel | 92 ± 42 | 75 ± 33 |
| Rt. Atrium-4% gel | 162 ± 89 | 147 ± 73 |
| Rt. Ventricle-control gel | 0 ± 0 | 0 ± 0 |
| Rt. Ventricle-1% gel | 24 ± 3 | N.A. |
| Rt. Ventricle-4% gel | 86 ± 6 | 70 ± 14 |

N.A. = sample not available.

These results demonstrate that FOCALSEAL-S delivers therapeutically-relevant levels ($\geq 20$ µg/g tissue) of amiodarone to pig myocardium over 7 days. Atrial tissue under 1% and 4%-amidarone-loaded gels contained 84 and 155 µg/g tissue, respectively. Ventricle myocardium under 1% and 4% gels showed 24 and 78 µg/g tissue, respectively.

While adjacent lung samples showed the presence of amiodarone, levels were much lower than those found in coated cardiac tissue.

EXAMPLE 8

Evaluation of FOCALSEAL-M® with Amiodarone and FOCALSEAL-S® with Amiodarone on Canine Cardiac Tissue This study was designed to evaluate the adherence of FOCALSEAL-M® and FOCALSEAL-S® macromer solutions with and without amiodarone on a canine heart. Drug loaded FOCALSEAL-S® or FOCALSEAL-M® macromer solutions were applied on the right atrium in 8 dogs (N=4 dogs/group) then photopolymerized in situ. All dogs received both control (0%) and 0.5% amiodarone-loaded hydrogel.

Hydrogel Adherence at 7 days

Gel adherence was scored using a 5-point scale as discussed above. Individual and average adherence scores for hydrogels are listed in Tables 5, respectively.

On the 0 to 4 adherence scale described above, control hydrogelss (no drug) received an average score of 3.4 and amiodarone-loaded hydrogels received an average score of 3.6. Hydrogels formed using FOCALSEAL-S® and FOCALSEAL-M® macromer solutions showed equivalent adherence.

TABLE 5

Average Adherence Scores ± S.D.

| MACROMER TYPE | CONTROL | TREATMENT |
|---|---|---|
| FOCALSEAL-S | 3.5 ± 0.0 | 3.6 ± 0.5 |
| FOCALSEAL-M | 3.4 ± 0.3 | 3.6 ± 0.3 |

Drug Analysis:

FOCALSEALFOCALSEALThe data show 31±8% amiodarone was released after 7 days in vivo implantation from hydrogel patches prepared with the FOCALSEAL-S™ and 37±10% was released from gel patches prepared with the FOCALSEAL-M™ macromer solutions.

This study determined the amiodarone concentrations in each dog's right atrial tissue under the drug-loaded hydrogels in the FOCALSEAL-S and FOCALSEAL-M treatment groups. Tissue under the FOCALSEAL-S drug-loaded hydrogel showed an average amiodarone concentration of 84±81 µg/g tissue; tissue under the FOCALSEAL-M hydrogel showed an average amiodarone concentration of 34±17 µg/g tissue. Analysis of the myocardial tissue under the control hydrogel and untreated area showed no detectable drug levels in any of the animals. In addition, no drug was detected in any of the distal cardiac or lung tissue samples.

EXAMPLE 9

Effect of FOCALSEAL-S™+Amiodarone (0.5% and 1%) on Dog Cardiac Tissue

A dog study was conducted as described in Example 8. Table 6 shows the average amiodarone concentrations in right atrial tissue beneath 0.5% and 1% amiodarone-loaded FOCALSEAL-S™.

The two 0.5% amiodarone-treated dogs showed an average amiodarone concentration of 94±24 µM. This result agrees well with the results observed in the study presented in Example 8. The cardiac tissues in two dogs treated with 1% amiodarone-loaded hydrogel had an average amiodarone concentration of 337±36 μM.

TABLE 6

Amiodarone Concentrations in Dog Atrium

| DOG # | GEL TREATMENT | [AMIODARONE] IN RIGHT ATRIUM (μM ± SD) |
|---|---|---|
| 1 | 0.5% amiodarone | 95 ± 34 |
| 2 |  | 93 ± 16 |
| 3 | 1% amiodarone | 343 ± 23 |
| 4 |  | 331 ± 51 |

None of the other tissue harvested (including right atrial appendage, right ventricle, left atrial appendage, left atrial free wall, left ventricle and distal lung) showed a detectable level of amiodarone in the tissue.

This study confirms the local delivery of the drug amiodarone at therapeutically relevant levels to the the right atrium of the canine heart using hydrogels polymerized from FOCALSEAL macromer solutions. The amount of drug delivered could be increased or decreased by increasing the initial loading of amiodarone into the macromer solutions. Detectable and therapeutically relevant drug levels were confirmed in the cardiac tissue at the site of application of the hydrogels.

EXAMPLE 10

Study of Electrophysiology of Amiodarone-Loaded Hydrogels on the Canine Heart

This study was designed to evaluate over time the effects on the atrial effective refractory period (AERP) of amiodarone-loaded hydrogels prepared from FOCALSEAL™ macromer solutions applied to the right atrium of canine heart tissue and photopolymerized. Hydrogels were evaluated for their electrophysiological effects at various time points (3–5 days, 10–15 days, and 3 weeks) at the following concentrations of amiodarone: 0% (control), 0.5% and 1%.

This study was conducted using 13 mongrel dogs weighing between 17–30 Kg. Under fluoroscopic guidance, using quadripolar catheters, drug-loaded hydrogel patches were deposited and photopolymerized following application of a priming solution as described earlier on the right atrium, the right ventricle and coronary sinus. Electrophysiological measurements were performed prior to thoracotomy and following thoracotomy closure at the time intervals set out above.

Table 7 show the changes (in %) in AERP of the canine heart tissue below the hydrogels within the control group and within the treated group (0.5% and 1% results combined).

TABLE 7

% Changes In AERP As A Function Of Time In Control And Treated Dogs

| Gel Patches (# dogs) | Pre-operative | Day 3–5 | Day 10–14 | 3–6 Weeks |
|---|---|---|---|---|
| Control (5) | 0.2 | 23.5 | 4.5 | −10.6 |
| Drug loaded (8) | 6.4 | 37 | 23.6 | 30.9 |

In summary, this study shows that the amiodarone-loaded patches on the atrium increases the effective refractory period of the atrium as compared to the control hydrogels free of the drug.

EXAMPLE 11

Inclusion of Hyaluronic Acid to Increase Viscosity of In Vivo Polymerized Macromer for Delivery of Drug 50 mg of 150 kDa sodium hyaluronate (HA) was added to a 10 g aqueous formulation consisting of 1 g FOCALSEAL™-S, 54 mg TEOA, 80 mg KPhos, 40 mg VC, and 0.4 mg of Eosin-Y to make a solution containing 1% HA. 2%, 3%, 4% and 5% HA FOCALSEAL™-S were similarly prepared.

Figure 5A:
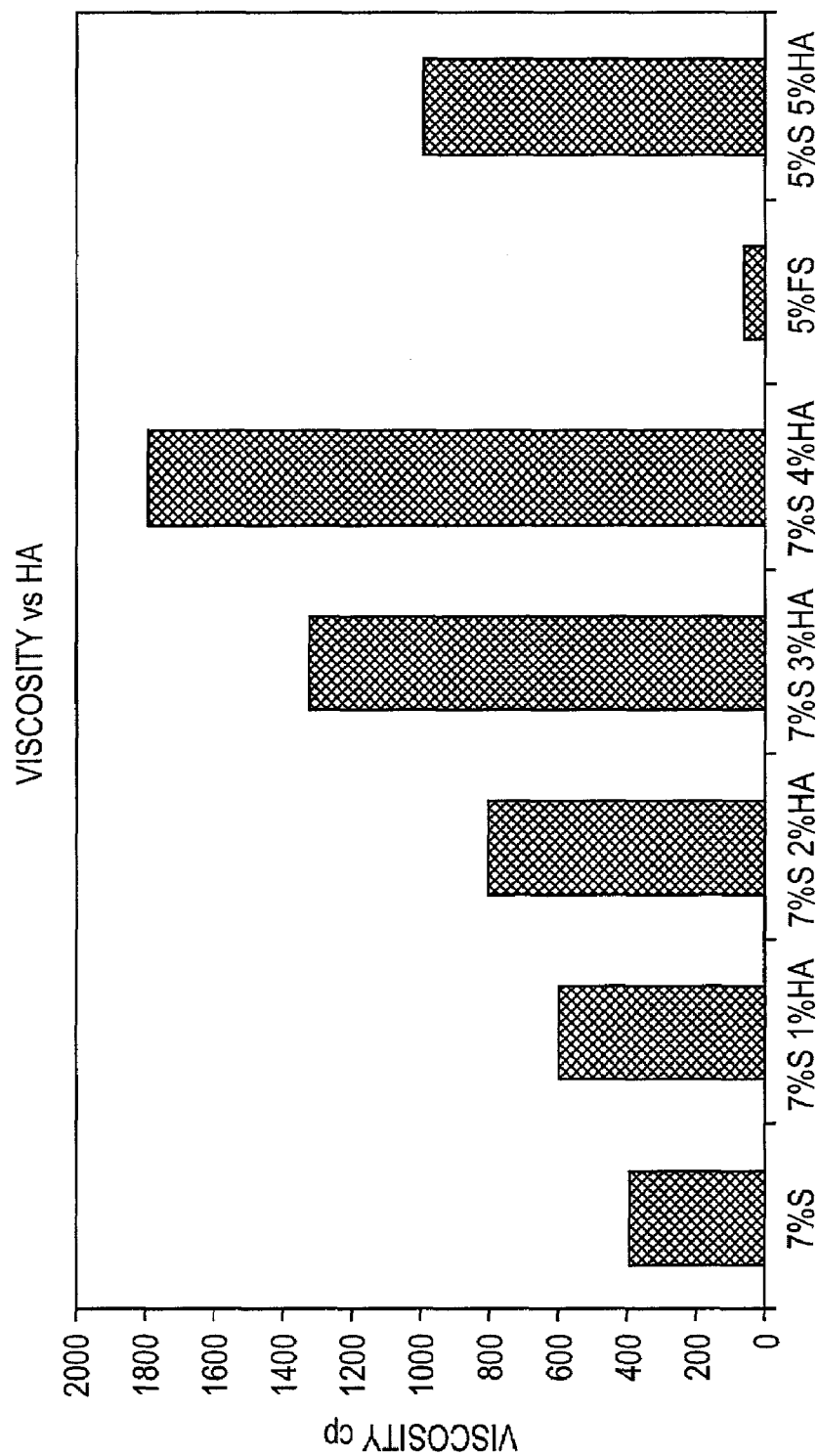
FIG. 5A is a graph of viscosity (cp) for 7% FOCALSEAL-S™, alone or in combination with 1%, 2%, 3%, or 4% HA, and 5% FOCALSEAL-S™, alone or in combination with 5% HA.
Figure 5B:
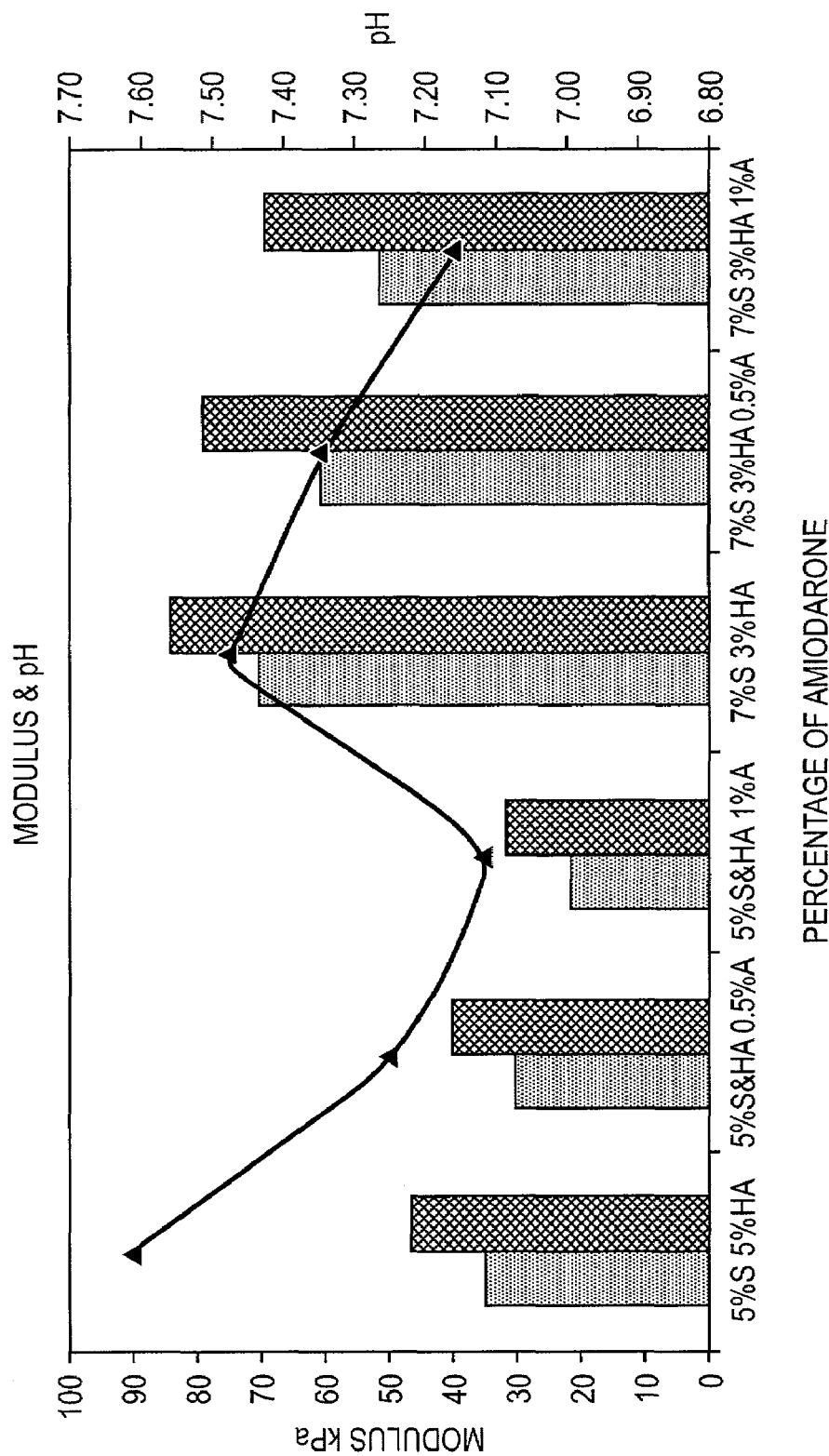
FIG. 5B is a graph of modulus (kPa) and pH of 5% FOCALSEAL-S™ in combination with 5% HA, alone or in further combination with 0.5% or 1% amiodarone, and 7% FOCALSEAL-S™ in combination with 3% HA, alone or in further combination with 0.5% or 1% amiodarone.

HA is added to modify the viscosities of the FOCALSEAL™-S solutions so that it remains at the site of application on the tissue where it is to be polymerized to form the hydrogel. As shown by FIG. 5A, the viscosities of the formulations with HA were significantly higher than the corresponding macromer formulations without the added HA. The moduli and pH of the solutions are shown by FIG. 5B.

These solution can then be applied to tissue and polymerized. For example, a first aqueous 5.028 g formulation prepared containing 0.9005 g FOCALSEAL™, 0.0302 g HA, 0.03 g ferrous gluconate (Fe-Gluconate), and 25 μL VC, and a second aqueous 5.028 g formulation is prepared containing 0.9005 g FOCALSEAL™, 0.0302 g HA, 126.3 ppm t-Butylperoxide, and 25 μL VC, loaded into separate syringes, and placed in a dual syringe holder. A device containing a 1 inch-long static mixer is attached to the end of the syringes. When the aqueous solutions are released from the syringes in a 1:1 ratio, the mixture gels almost instantaneously.

The polymerized hydrogels were tested for adherence in the explanted pig lung inflation model. Two formulations were tested: 5% FOCALSEAL-S™ containing 5% by weight HA, and 7% FOCALSEAL-S™ containing 3% by weight HA, each with either 0.5% or 1% by weight amiodarone. The adherence score at 40 hrs for the first composition was 3 and for the second composition 3.5.

It is understood that the disclosed methods and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims. Those skilled in the art will recognize, or be able to ascertain using no more than routine experimentation, many equivalents to the specific embodiments of the invention described herein. Such equivalents are intended to be encompassed by the following claims.

We claim:

1. A liquid formulation comprising
1) an aqueous solvent comprising at least 50% by weight of water,
2) dispersed or solubilized within the solvent, biocompatible, biodegradable, synthetic, water soluble and covalently reactive macromers polymerizable to form a compliant tissue adhesive hydrogel degrading in a period of less than one month after application to the tissue, said macromers comprising on average per molecule at least one hydrophilic domain, at least one biodegradable region comprising carbonate linkages, and at least two polymerizable groups, 3) dispersed within the formulation, particles of an anti-arrhythmic agent in a dosage effective to lengthen atrial effective refractory period, where the anti-arrhythmic agent is selected from the group consisting of lidocaine, moricizine, mexiletine, tocainide, procainamide, encainide, flecanide, phenytoin, propafenone, quinidine, disopyramide, flecainide, propranolol, esmolol, amiodarone, artilide, bretylium, clofilium, isobutilide, sotalol, azimilide, dofetilide, dronedarone, ersentilide, ibutilide, tedisamil, trecetilide, verapamil, diltaizem, digitalis, adenosine, nickel chloride, and magnesium, and 4) a polymerization initiator.

2. The solution of claim 1 comprising macromers comprising a hydrophilic domain of polyethylene oxide, biodegradable linkages degrading in a period of less than about two weeks following application to the tissue, and capped with acrylate groups.

3. The solution of claim 2 wherein the biodegradable linkages are a combination of monomers or oligomers of carbonates and hydroxy acids.

4. The solution of claim 1 wherein the anti-arrhythmic agent is selected from the group consisting of amiodarone, sotalol and dronedarone.

5. The solution of claim 1 in a kit further comprising reagents for priming the surface of the tissue to which the solution is to be applied, wherein the priming increases the adhesion of the hydrogel to the tissue.

6. The solution of claim 1 further comprising a viscosity modifying agent.

7. The solution of claim 6 wherein the viscosity modifying agent is selected from the group consisting of glycosaminoglycans, carboxymethyl cellulose, dextran, dextran sulfate, and polyvinylpyrrolidone.

* * * * *